United States Patent [19]

Donike et al.

[11] Patent Number: 4,538,013

[45] Date of Patent: Aug. 27, 1985

[54] PROCESS FOR PRODUCING DIELS-ALDER ADDUCTS WHILE INHIBITING THE FORMATION OF POLYMERIC BY-PRODUCTS

[75] Inventors: Wilhelm Donike, Marl; Helmut Ulrich, Dorsten; Heinz Thiemer, Marl; Josefa Pieper, Haltern, all of Fed. Rep. of Germany

[73] Assignee: Chemische Werke Huls AG, Marl, Fed. Rep. of Germany

[21] Appl. No.: 585,471

[22] Filed: Mar. 2, 1984

[30] Foreign Application Priority Data

Mar. 3, 1983 [DE] Fed. Rep. of Germany ....... 3307486

[51] Int. Cl.$^3$ ................................................ C07C 3/00
[52] U.S. Cl. ..................... 585/361; 585/950; 526/83; 526/84
[58] Field of Search ............... 585/361, 360, 950; 526/83, 84

[56] References Cited

U.S. PATENT DOCUMENTS 2,752,403  6/1956  Schutze et al. ..................... 585/361
4,079,091  3/1978  Matsuno ............................. 585/361

FOREIGN PATENT DOCUMENTS 1327594  9/1973  United Kingdom ................ 585/361
1492901  11/1977  United Kingdom ................ 585/361

OTHER PUBLICATIONS

Chemical Abstract 84: 150176k, (Kisaki et al.).
Chemical Abstract 85: 63629n, (Watson).
Chemical Abstract 86: 44221c, (Watson).
Chemical Abstract 89: 44276m, (Li et al.).

Primary Examiner—D. E. Gantz
Assistant Examiner—A. Pal
Attorney, Agent, or Firm—Millen & White

[57] ABSTRACT

A process for preventing the formation of polymeric by-products during the production of Diels-Alder adducts is improved by the addition of NO or of a compound splitting off NO in situ, as a polymerization inhibitor. This process is especially effective for preventing the formation of polymeric by-products in the manufacture of 5-vinylnorbornene-2. In a tubular reactor, when observing narrow temperature and pressure ranges, a high selectivity is obtained in the production of this adduct.

9 Claims, No Drawings

PROCESS FOR PRODUCING DIELS-ALDER ADDUCTS WHILE INHIBITING THE FORMATION OF POLYMERIC BY-PRODUCTS

BACKGROUND OF THE INVENTION

It has been known for some time that undesirable formation of polymeric by-products in the preparation of Diels-Alder adducts could be prevented by adding certain polymerization inhibitors. Such formation of by-products is thus more or less extensively impeded, depending on whether the process is conducted discontinuously or continuously.

British Pat. No. 1,492,901 discloses the most recent and heretofore most advantageous prior art process and also provides a discussion of the earlier state of the art. The patent teaches the use of certain p-phenylenediamine compounds as polymerization inhibitors. They are to be added preferably in an amount of 50-500 ppm (weight/weight), based on the sum total of diene component and dienophilic component. The cost of manufacturing these p-phenylenediamine compounds is comparatively high, which makes their use a burden on the economics of the disclosed process.

A need therefore continues to exist for more economical inhibitors of polymeric by-products which nevertheless are compatible with the reactants, products and conditions of the Diels-Alder reaction.

OBJECTS OF THE INVENTION

One object of the invention is to provide a process for producing Diels-Alder adducts with minimal by-product formation, the process being more economical than the aforementioned closest prior art process.

Upon further study of the specification and appended claims, further objects and advantages of this invention will become apparent to those skilled in the art.

SUMMARY OF THE INVENTION

These objects are attained, in a process for preparing Diels-Alder adducts from (1) a diene component, being a conjugated diene capable of adduct formation, a diene precursor capable of liberating said diene in situ, or a mixture thereof, and (2) a dienophile, being an olefin, other than an alkyl allene, having an activated double bond capable of reacting with said diene to form said Diels-Alder adduct; wherein said diene component and said dienophile are reacted, at a temperature of 120°–250° C., with exclusion of oxygen, and in the presence of an effective polymerization inhibiting amount of a polymerization inhibitor, and resultant Diels-Alder adduct is recovered, by the improvement wherein the polymerization inhibitor is nitric oxide (NO), a nitric oxide precursor capable of liberating NO in situ, or a mixture thereof.

DETAILED DISCUSSION

The process of the invention uses conventional dienes and dienophiles which are well known to those skilled in the art relating to production of Diels-Alder adducts.

Suitable dienophilic components include, e.g., conjugated diolefins, especially acyclic 1,3-dienes, as well as olefins having an ethylenic double bond flanked by carbonyl or carboxyl groups. The use of 1,3-butadiene is particularly preferred.

Alkyl allenes are disclosed as dienophiles in British Pat. No. 1,327,594. However, their use has been fraught with danger in that explosions may result. Accordingly, they are excluded from the scope of the present invention.

The diene component is conventional.

Preferred dienes include cyclic dienes, e.g., cyclopentadiene, or diene precursors, e.g., dicyclopentadiene, capable of liberating dienes under the reaction conditions.

The reaction is carried out with exclusion of oxygen, e.g., in an inert gas atmosphere, e.g., nitrogen. It will be appreciated that commercially available nitrogen, or other inert gases, may contain a small amount of residual oxygen as a contaminant, e.g., about 10 ppm (volume/volume), which does not materially affect the results.

The polymerization inhibitor is NO or another convenient source thereof. Suitable such sources are compounds which are capable of liberating NO in situ under the reaction conditions, e.g., $N_2O_3$. NO itself is an inexpensive, commercially available gas.

The inhibitor is added to the reaction mixture in an amount effective to inhibit formation of polymeric by-products. A suitable amount generally ranges from 25 to 1000 ppm, preferably 50-500 ppm (weight/weight), of inhibitor, calculated as NO, relative to the total combined weight of diene and dienophile components.

The Diels-Alder reaction can be carried out, according to the invention, by combining the reactants and the inhibitors, under conventional conditions and in conventional proportions. The dependence of selectivity in the preparation of the adducts on the molar ratio and on the conversion rates of the components is basically known to persons skilled in the art, as disclosed in, e.g., German Pat. No. 2,161,215 and East German Pat. No. 94,175. Optionally, the reaction can be effected in a suitable inert organic solvent conventionally used in the art.

The process of this invention is especially advantageous because it can be carried out continuously for a long period of time without the occurrence of undesirable polymer. Thus, reactor components, heat exchangers, ducts and the like, are not clogged or coated with polymer buildup.

The detailed mechanism by which the polymerization inhibitor of this invention works has not been elucidated. While not being bound by any particular mechanism, it appears that the inhibitor is capable of preventing the polymerization of the diene components and of the dienophilic components, especially the polymerization of acyclic 1,3-dienes, as well as the polymerization of the cycloolefinic adducts, as illustrated in the examples.

In a preferred embodiment of the present process, the diene component is cyclopentadiene and/or dicyclopentadiene, and the dieneophile is 1,3-butadiene. Dicyclopentadiene liberates 2 moles of cyclopentadiene in situ at or above 160° C. When cyclopentadiene alone is the diene, the reaction temperature is preferably 140°–220° C., and when the diene component is dicyclopentadiene, alone or mixed with cyclopentadiene, the reaction temperature is preferably 160°–220° C. The Diels-Alder adduct in this case is 5-vinylnorbornene-2 (5-vinylbicyclo[2.2.1]hept-2-ene).

5-Vinylnorbornene-2 is a commercially important compound. It can be conventionally isomerized to 5-ethylidene-2-norbornene, the latter being a diene having unconjugated olefinic double bonds of differing reactivity (popularly denoted a "termonomer") useful for producing vulcanizable ethylene-propylene-termonomer (EPDM) elastomers.

In a further preferred embodiment, cyclopentadiene and/or dicyclopentadiene, 1,3-butadiene, and NO or an NO precursor are reacted in a continuous process, preferably at 160°–210° C. and an absolute pressure in the reactor of 5–20 bar. More preferably, continuous reaction is effected in a tubular reactor, at 170°–210° C. and an absolute pressure of 11–15 bar, most preferably 12–14 bar.

The latter process permits production of the adduct with high yield based on the reacted components, i.e. with high selectivities, since there is not only a prevention of the formation of polymeric by-products in accordance with the object of this invention, but there is also a restriction of the formation of oligomeric and low molecular weight by-products, e.g., 4-vinylcyclohexene-1 and tetrahydroindene. The high selectivities result, inter alia, from the fact that there is always a mixed phase in the indicated, narrow temperature and pressure ranges, this being understood to mean the existence of both a gaseous phase and a liquid phase.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight. In the examples, ppm means ppm, weight/weight, unless otherwise indicated.

EXAMPLES 1 AND 2

Preparation of 5-Vinylnorbornene-2

Under nitrogen (10 ppm, volume/volume, oxygen), a 3-liter agitator-equipped autoclave (stainless steel) was charged with respectively 500 g of 1,3-butadiene and dicyclopentadiene molar ratio of 1,3-butadiene/cyclopentadiene=1.2:1), and with the amounts of NO indicated in the table. The contents of the reactor were maintained at 176° C. for 5 hours. The initial pressure at 176° C. was 20 bar (absolute). After 5 hours, the absolute pressure was about 10 bar. After cooling, the reactor content and the inner surfaces of the reactor were analyzed.

TABLE

| Example | NO [ppm] | Evaluation |
|---|---|---|
| 1 | 100 | Clear liquid, no deposits |
| 2 | 1,000 | As in Example 1 |

EXAMPLE 3

Preparation of 5-Vinylnorbornene-2 (continuous)

In a tubular reactor, the volume of which was 1.2 liter, the air was displaced by butane. Then the reactor was charged with a mixture of 1,3-butadiene, dicyclopentadiene (weight ratio 1.5:1; molar ratio of 1,3-butadiene/cyclopentadiene=1.8:1) and 100 ppm of NO at a rate of 1.2 kg/h. During this step, the mixture was heated to 180° C. in the inlet zone of the reactor and maintained at this temperature in the reaction zone. The absolute pressure in the reactor was 12 bar.

After 300 hours, the experiment was terminated. The discharge from the reactor was a clear fluid during the entire operating period. No deposits could be found on the inner surfaces of the reactor.

Conversion of 1,3-butadiene: 20.6%
Conversion of dicyclopentadiene: 65.5%
Yield of 5-vinylnorbornene-2: 54% of theory, based on reacted 1,3-butadiene. The yield was determined by distillative separation of the reactor product in three fractions and gas-chromatographic analysis of vinylnorbornene and unreacted 1,3-butadiene in the fractions.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In a process for preparing 5-vinylnorbornene-2 by the Diels-Alder reaction of 1,3-butadiene with cyclopentadiene, dicyclopentadiene or a mixture thereof, at a temperature of 120°–250° C., with exclusion of oxygen, and in the presence of an effective polymerization inhibiting amount of a polymerization inhibitor, and recovering the 5-vinylnorbornene-2 thereby prepared, the improvement wherein said polymerization inhibitor is nitric oxide (NO), a nitric oxide precursor capable of liberating NO in situ, or a mixture thereof.

2. A process according to claim 1, wherein said effective amount of inhibitor, calculated as NO, is 25–1000 ppm by weight, based on the total weight of diene and dienophile.

3. A process according to claim 2, wherein said amount is 50–500 ppm.

4. A process according to claim 1, wherein said polymerization inhibitor is NO.

5. A process according to claim 1, wherein said reaction is effected continuously, said reaction temperature is 160°–210° C., and the absolute pressure in the reaction zone is 5–20 bar.

6. A process according to claim 5, wherein said reaction is effected in a tubular reactor, said reaction temperature is 170°–210° C., and said absolute pressure is 11–15 bar.

7. A process according to claim 6, wherein said absolute pressure is 12–14 bar.

8. A process according to claim 1, wherein said diene component is cyclopentadiene; and said reaction temperature is 140°–220°C.

9. A process according to claim 1, wherein said diene component is dicyclopentadiene or a mixture of cyclopentadiene and dicyclopentadiene; and said reaction temperature is 160°–220° C.

* * * * *